United States Patent
Heinzelmann et al.

(10) Patent No.: US 6,335,365 B1
(45) Date of Patent: Jan. 1, 2002

(54) FIREPROOF, NON-EXPLODING NITROGLYCERINE AND SOLID MIXTURES CONTAINING ANHYDROUS LACTOSE

(75) Inventors: Walter Heinzelmann, Odenthal; Cornelius Ruloff, Leverkusen, both of (DE)

(73) Assignee: Dynamit Nobel GmbH Explosivstoff-und Systemtechnik, Troisdorf (DE)

(*) Notice: Subject to any disclaimer, the term of this patent is extended or adjusted under 35 U.S.C. 154(b) by 0 days.

(21) Appl. No.: 09/300,593

(22) Filed: Apr. 28, 1999

(30) Foreign Application Priority Data

Apr. 29, 1998 (DE) .............................................. 198 19 012

(51) Int. Cl.[7] .............................. A61K 31/21; A61L 9/02
(52) U.S. Cl. .............................................. 514/509; 424/42
(58) Field of Search ................................ 424/42, 19, 440, 424/400, 489, 80, 472, 453; 514/41, 152, 159, 162, 509

(56) References Cited

U.S. PATENT DOCUMENTS

| | | | | |
|---|---|---|---|---|
| 3,432,593 A | | 3/1969 | Shepard | |
| 4,059,686 A | * | 11/1977 | Tanaka et al. | 424/435 |
| 4,073,931 A | * | 2/1978 | Akito et al. | 514/509 |
| 4,091,091 A | | 5/1978 | Terrill | |
| 4,481,220 A | * | 11/1984 | Giesselmann et al. | 514/788 |
| 4,654,209 A | * | 3/1987 | Leslie et al. | 424/80 |
| 4,921,695 A | * | 5/1990 | Babaian et al. | 424/449 |
| 5,573,777 A | * | 11/1996 | Serpelloni | 424/440 |
| 5,674,530 A | * | 10/1997 | Amidon et al. | 424/472 |
| 5,895,663 A | * | 4/1999 | Irwin et al. | 424/468 |

OTHER PUBLICATIONS

Drug and Facts Comparison–1997 edition, Nitroglycerin product, p. 721.*

* cited by examiner

Primary Examiner—William R. A. Jarvis
Assistant Examiner—Vickie Kim
(74) Attorney, Agent, or Firm—Antonelli, Terry, Stout & Kraus, LLP

(57) ABSTRACT

The present invention relates to fireproof, non-explosive solids mixtures containing nitroglycerin and anhydrous lactose that do not have to be classified as an explosive in accordance with ADR/RID, IATA, IMCO and/or UN guidelines, to methods for the preparation of such solids mixtures and to the use of anhydrous lactose for the preparation of fireproof, non-explosive solid mixtures containing nitroglycerin and lactose that do not have to be classified as an explosive in accordance with ADR/RID, IATA, IMCO and/or UN guidelines.

5 Claims, No Drawings

FIREPROOF, NON-EXPLODING NITROGLYCERINE AND SOLID MIXTURES CONTAINING ANHYDROUS LACTOSE

This application claims priority under 35 U.S.C. § 119 of Germany-198 19012.3, filed Apr. 29, 1998.

The subject-matter of the present invention is the use of lactose as excipient of nitroglycerin.

Nitroglycerin (glyceryl trinitrate, propantriol-1,2,3-trinitrate) is a well-known liquid nitrate ester which has found widespread use as an active ingredient of a drug in numerous medicaments for coronary therapy that can be formulated both for a fast action in emergency cases and for a slow release of the active ingredient for an extended protection against angina pectoris attacks.

Depending on the composition of medicaments for important fields of use in coronary therapy, for example for oral, dermal or parenteral use, the availability of nitroglycerin for pharmaceutical production purposes presents a constant problem. As a highly explosive active ingredient, nitroglycerin can be made available for handling and transport only in the form of concentrates which are fully stabilised and safe to handle or as finished medicaments in bulk form, which can be produced only under safe conditions in an explosives factory and using suitable inert carrier materials as excipients, which have to be selected in accordance with the particular physical-chemical properties of the nitroglycerin and need to have been the subject of pharmacopoeia monographs.

Different types of drugs which contain nitroglycerin require different types of excipients for the incorporation of nitroglycerin in order for products to be obtained which, even under extreme conditions, for example under the effect of flames in the case of a fire, must be absolutely safe to handle during production, packaging, storage, transportation and final use.

Mainly practical requirements have led to the development of two different groups of stabilised concentrates which are already commercialised and serve as master batches for further processing:

Group A: formulation of nitroglycerin in liquid excipients, for example in:
alcohols,
medium-chain triglycerides,
plant or synthetic oils,
organic solvents,
organic polymers (solutions, dispersions).

Group B: formulations of nitroglycerin in solid excipients, for example in:
sugars and polysaccharides,
cellulose and derivatives,
polymeric materials,
inorganic excipients.

Among the materials contained in group B, having commercial interest as pharmaceutical intermediate products which have many uses, for example for the preparation of tablets, capsules, ointments or plasters are, in particular, solid concentrates of nitroglycerin in sugars, such as lactose for example.

Decisive for the granting of a transport permit by national and/or international transport authorities are the results of safety tests and material safety data obtained according to nationally and/or internationally introduced safety-standard testing methods and in accordance with legal requirements, as stipulated by ADR/RID, IATA, IMCO and UN guidelines and by the associated test manuals.

Decisive for the classification of a substance as an explosive or as a non-explosive are the results of certain tests which are to be carried out in order to determine the parameters mentioned below:

sensitivity to heat when confined, according to the Koenen test; UN test handbook, series 2 (b), "Koenen test";

detonation susceptibility according to the 2" steel tube test; UN test handbook, test A, series A.1, BAM 50/60 "steel tube";

impact sensitivity according to the drop-hammer test; UN test handbook, test 3 (a)(i), "BAM drop-hammer";

friction sensitivity according to the BAM friction test; UN test handbook, test 3 (b)(i), "BAM friction apparatus";

sensitivity to heat according to the "bonfire test" using original storage and transport containers; UN test handbook, "external fire (bonfire) test", series 6 (c).

Limiting values are specified for each test, which limiting values must not be exceeded by non-explosives. If, however, these limiting values are exceeded even in only one single test, for example during the "Koenen test" and/or the "bonfire test", the material which is tested is to be classified as an explosive. Non-explosives on the other hand are further subjected to the required classifications as hazardous goods, such as, for example, in class 3 (inflammable), in class 4.1 (inflammable solid materials) or in class 6 (poisonous).

A typical, commercially available standard bulk formulation of nitroglycerin with solid excipients is, for example, the solid mixture of 10% by weight nitroglycerin ($C_3H_5N_3O_9$) in 90% by weight lactose monohydrate ($C_{12}H_{22}O_{11} \cdot 1\ H_2O$). This formulation was also tested with the above-mentioned testing program. While the "Koenen test", the "steel tube test", the "BAM drop-hammer test" and the "BAM friction apparatus test" resulted in values below the respective limiting value, the "bonfire test" led to violent explosions. When the original packing drums for transport and storage, in which 50 kg (net) of the solid mixture of nitroglycerin and lactose monohydrate was packed into 100 l fibre barrels with polyethylene bag liners, were exposed to open flames for a comparatively long time, a violent explosion was regularly observed after approximately 45 mins.

For this reason, this commercially available standard bulk formulation of 10% by weight nitroglycerin in 90% by weight lactose monohydrate has been classified by the national and international transport authorities as an explosive in class 1.1 D. Production, storage and in particular transport activities are therefore so heavily handicapped by legislative restrictions that the material is practically excluded from international transport. Thus, there is a general ban on air shipments for this material; shipments by road, train and sea can be carried out only as explosives shipments; there are restrictions on quantity per individual package and total cargo amount; the freight costs are extremely high; individual permits are required for each shipment in transit; depending on the recipient country, special demands are additionally placed on buildings (warehouses, production) and the devices for further processing; specially trained and licensed personnel are required; the possibilities for sale are heavily restricted.

Even the addition of small amounts of additives, for example finely-dispersed silicon dioxide (Aerosil), alkali or alkaline earth carbonates, alkali or alkaline earth bicarbonates, alkali or alkaline earth hydroxides or alkali or alkaline earth oxides (U.S. Pat. No. 428,378; EP-A-0 104 877) had no influence on the results of the relevant tests for testing the sensitivity to heat, for example the steel-plate box test, and could not prevent the explosion.

The object of the present invention was therefore to make available a solids mixture for nitroglycerin, which mixture has no risk of explosion but instead high thermal stability and therefore does not need to be classified as an explosive.

Surprisingly, it was possible to prepare a fireproof, non-explosive solids mixture containing nitroglycerin by using anhydrous lactose as excipient for nitroglycerin, and thus achieve the underlying object of the invention.

Tests on the reactions occurring during the explosion in the "bonfire test" by means of thermogravimetric analysis (TGA) have shown that in the case of raised temperatures, the lactose monohydrate, which has hitherto been used as excipient for the adsorption of nitroglycerin, releases its water of crystallisation within a temperature range from 100° C. to 150° C. with subsequent melting above 215° C. Because of this effect, the nitroglycerin which is adsorbed on lactose monohydrate and is practically insoluble in water is washed off and separated from the crystal surfaces of the lactose monohydrate by the water (steam/condensate) which is released. This, however, changes the safety status of the solid mixture which was previously fully stabilised at ambient temperatures. As a result of migration and concentration of the nitroglycerin as liquid phase, the mixture changes into a highly explosive material which explodes under the conditions of the "bonfire test". These results were also supported and substantiated by the subsequent tests on the places of the explosion and pieces of debris.

The thermal safety of solids mixtures which contain nitroglycerin and lactose can now surprisingly be improved significantly as a result of the fact that instead of lactose monohydrate as excipient, anhydrous lactose is used for the adsorption of nitroglycerin.

The solids mixtures in accordance with the invention are prepared in a commercially available standard mixer, for example in a planetary-type mixer, in which dry anhydrous lactose in accordance with EP, USP, JP is placed and, whilst stirring, pure nitroglycerin is added from a suitable dosing device. After the end of the addition, the mixture is stirred for a further period of time, preferably at least two hours. The homogeneous solids triturate of nitroglycerin in anhydrous lactose that is obtained in this way is packed into fibre barrels with polyethylene bag liners and stored in the dry at room temperature.

Even tests on solids mixtures in accordance with the invention that contained $\geq 10\%$ by weight nitroglycerin with corresponding amounts of anhydrous lactose resulted, in all of the above-mentioned tests, in values which were clearly below the respective limiting values. Even in the burning test, the solids mixtures in accordance with the invention did not lead to explosions.

Series of tests for testing the sensitivity to heat have shown that the available margin for the thermal safety (in the case of fire) permits an increase in the nitroglycerin proportion to far above 10% by weight nitroglycerin with the corresponding amount of anhydrous lactose.

The fireproof non-explosive solids mixtures in accordance with the invention that contain nitroglycerin and anhydrous lactose do not have to be classified as an explosive in accordance with ADR/RID, IATA, IMCO and/or UN guidelines. Accordingly, they must count as explosion-proof material.

The present invention relates in detail to:

fireproof, non-explosive solids mixtures containing nitroglycerin and anhydrous lactose. These solids mixtures in accordance with the invention do not have to be classified as an explosive in accordance with ADR/RID, IATA, IMCO and/or UN guidelines. They preferably contain a mixture of (4+x)% by weight nitroglycerin and (96-x)% by weight anhydrous lactose, with respect to the mixture of nitroglycerin/anhydrous lactose, where x can assume values of 0 to 9, preferably the values 4, 6 or 8.

Furthermore, the invention relates to the use of anhydrous lactose for the preparation of fireproof solids mixtures containing nitroglycerin and lactose, in particular the use of (96-x)% by weight anhydrous lactose and (4+x)% by weight nitroglycerin, with respect to the mixture of nitroglycerin/anhydrous lactose, where x can assume values of 0 to 9, preferably the values 4, 6 or 8.

Furthermore, the invention relates to methods for the preparation of fireproof solids mixtures containing nitroglycerin and lactose, in which anhydrous lactose and nitroglycerin, in particular (96-x)% by weight anhydrous lactose and (4+x)% by weight nitroglycerin, with respect to the mixture of nitroglycerin/anhydrous lactose, are mixed homogeneously, where x can assume values of 0 to 9, preferably the values 4, 6 or 8.

Studies for determining the LD 50 values of the acute oral toxicity and the acute dermal toxicity of solid mixtures of 10% by weight nitroglycerin and 90% by weight lactose on rats gave values of >2000 mg/kg in each case. A classification of this material in class 6 (very poisonous) is therefore likewise unnecessary.

What is claimed is:

1. Fireproof, non-explosive solids mixture containing nitroglycerin and anhydrous lactose, characterised in that it contains a mixture of (4+x)% by weight nitroglycerin and (96-x)% by weight anhydrous lactose, with respect to the mixture of nitroglycerin/anhydrous lactose, where x can assume values of 0 to 9.

2. Fireproof, non-explosive solids mixture containing nitroglycerin and anhydrous lactose in accordance with claim 1, characterised in that it contains 13% by weight nitroglycerin and 87% by weight anhydrous lactose, with respect to the mixture of nitroglycerin/anhydrous lactose.

3. Method for the preparation of a fireproof, non-explosive solids mixture containing nitroglycerin and lactose, characterised in that (96−x)% by weight anhydrous lactose and (4+x)% by weight nitroglycerin, with respect to the mixture of nitroglycerin/anhydrous lactose, are mixed homogeneously, where x can assume values of 0 to 9.

4. Method in accordance with claim 3, characterised in that X assumes the value 4, 6 or 8.

5. Fireproof, non-explosive solids mixture in accordance with claim 1, characterised in that X assumes the value 4, 6 or 8.

* * * * *